(12) United States Patent
Maack et al.

(10) Patent No.: US 9,472,007 B2
(45) Date of Patent: Oct. 18, 2016

(54) FREQUENCY DEPENDENT COMBINATION OF X-RAY IMAGES OF DIFFERENT MODALITIES

(75) Inventors: Hanns-Ingo Maack, Norderstedt (DE); Ewald Roessl, Ellerau (DE); Thomas Koehler, Norderstedt (DE); Roland Proska, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 192 days.

(21) Appl. No.: 14/236,668

(22) PCT Filed: Jul. 27, 2012

(86) PCT No.: PCT/IB2012/053854
§ 371 (c)(1),
(2), (4) Date: Feb. 3, 2014

(87) PCT Pub. No.: WO2013/027138
PCT Pub. Date: Feb. 28, 2013

(65) Prior Publication Data
US 2014/0169653 A1    Jun. 19, 2014

Related U.S. Application Data

(60) Provisional application No. 61/525,381, filed on Aug. 19, 2011.

(51) Int. Cl.
*G06K 9/00* (2006.01)
*G06T 11/60* (2006.01)
(Continued)

(52) U.S. Cl.
CPC .............. *G06T 11/60* (2013.01); *A61B 6/484* (2013.01); *G06T 5/50* (2013.01);
(Continued)

(58) Field of Classification Search
None
See application file for complete search history.

(56) References Cited

U.S. PATENT DOCUMENTS 5,488,674 A * 1/1996 Burt ........................ G06T 5/50
345/639
6,016,356 A * 1/2000 Ito ........................ G06T 5/004
382/132

(Continued)

FOREIGN PATENT DOCUMENTS

EP    1879020    1/2008

OTHER PUBLICATIONS

E. Roessl et al., "Image Fusion Algorithm for Differential Phase Contrast Imaging", Medical Imaging 2012: Physics of Medical Imaging, Proc. of SPIE, vol. 8313, pp. 831354-1 through 831354-6.
(Continued)

*Primary Examiner* — Wenpeng Chen (57) ABSTRACT

In phase-contrast imaging, different types of image information, such as absorption image information and differential phase-contrast image information, may be obtained by a single image acquisition process and have different image properties. A frequency dependent combination of different types of image information is obtained, the combined image having improved properties over the image information and respective image information types. Accordingly, an apparatus and a method for image processing in X-ray imaging of an object is provided, including receiving first and second image information of the object of first and second image information types, respectively, where the second image information type is different from the first image information type. The first and second image information is combined to obtain combined image information of the object, where the combined image information is frequency-dependent, depending on spatial frequencies of the first and second image information, respectively.

11 Claims, 10 Drawing Sheets

(51) Int. Cl.
*G06T 5/50* (2006.01)
*A61B 6/00* (2006.01)

(52) U.S. Cl.
CPC ............... *G06T 2207/10116* (2013.01); *G06T 2207/20056* (2013.01); *G06T 2207/20221* (2013.01); *G06T 2207/30004* (2013.01)

(56) References Cited

U.S. PATENT DOCUMENTS

| | | | |
|---|---|---|---|
| 6,262,818 B1* | 7/2001 | Cuche | G03H 1/0443 359/10 |
| 7,054,474 B1* | 5/2006 | Krieger | G06T 5/002 348/241 |
| 2001/0038680 A1* | 11/2001 | Davidson | A61B 6/484 378/43 |
| 2005/0264813 A1* | 12/2005 | Giakos | B82Y 20/00 356/369 |
| 2006/0039532 A1* | 2/2006 | Wu | A61B 6/484 378/62 |
| 2006/0291707 A1 | 12/2006 | Kothapalli | |
| 2007/0255535 A1 | 11/2007 | Marro | |
| 2007/0274435 A1* | 11/2007 | Ning | A61B 6/032 378/4 |
| 2009/0074275 A1* | 3/2009 | O Ruanaidh | G06T 7/0081 382/128 |
| 2009/0161935 A1* | 6/2009 | Bruder | A61B 6/481 382/131 |
| 2009/0208080 A1* | 8/2009 | Grau | G06T 5/50 382/131 |
| 2010/0034441 A1* | 2/2010 | Makram-Ebeid | A61B 6/481 382/128 |
| 2010/0220832 A1* | 9/2010 | Ning | A61B 6/032 378/4 |
| 2010/0220834 A1 | 9/2010 | Heismann | |
| 2010/0322497 A1* | 12/2010 | Dempsey | G01R 33/4826 382/131 |
| 2011/0220791 A1* | 9/2011 | Reed | H01J 37/04 250/307 |
| 2011/0268328 A1* | 11/2011 | Bar-Aviv | G06T 5/50 382/128 |
| 2012/0002854 A1* | 1/2012 | Khare | G06T 11/006 382/131 |
| 2012/0237104 A1* | 9/2012 | Fouras | A61B 5/08 382/132 |
| 2013/0202177 A1* | 8/2013 | Bar-Aviv | G06T 11/008 382/131 |

OTHER PUBLICATIONS

L. Yang et al., "Multimodality Medical Image Fusion Based on Multiscale Geometric Analysis of Countourlet Transform", Neurocomputing 72 (2008) pp. 203-211.

* cited by examiner

FREQUENCY DEPENDENT COMBINATION OF X-RAY IMAGES OF DIFFERENT MODALITIES

CROSS-REFERENCE TO PRIOR APPLICATIONS

This application is the U.S. National Phase application under 35 U.S.C. §371 of International Application Serial No. PCT/IB2012/053854, filed on Jul. 27, 2012, which claims the benefit of U.S. Provisional Application Ser. No. 61/525,381, filed on Aug. 19, 2011. These applications are hereby incorporated by reference herein.

FIELD OF THE INVENTION

The invention relates to X-ray imaging technology as well as image post-processing in general.

In particular, the present invention relates to an apparatus and a method for image processing in X-ray imaging of an object.

Particularly, the present invention relates to combining different X-ray image information types, substantially concurrently acquired, depending on the frequency of the respective image information type, in particular depending on the spatial frequency of the image information.

BACKGROUND OF THE INVENTION

In general X-ray imaging, an object is examined by taking absorption measurements of X-radiation penetrating the object of interest. While fine absorption differences within the object may be displayed with sufficient detail, areas within the object having a similar chemical composition, thereby having a similar absorption characteristics, may only be displayed with unsatisfactory detail.

Advancements in X-ray imaging technology provided phase-contrast imaging techniques taking into account the phase-shift of X-radiation passing through an object, which regularly is substantially stronger than a corresponding absorption. Interferometric measurement methods are employed to measure such a phase-shift of X-radiation within an object by irradiating the object with coherent X-radiation, while using a pair of gratings between the object and an X-ray detector to ultimately obtain phase information by using the grating pair to perform what is known in the art as phase stepping.

Figure 1:
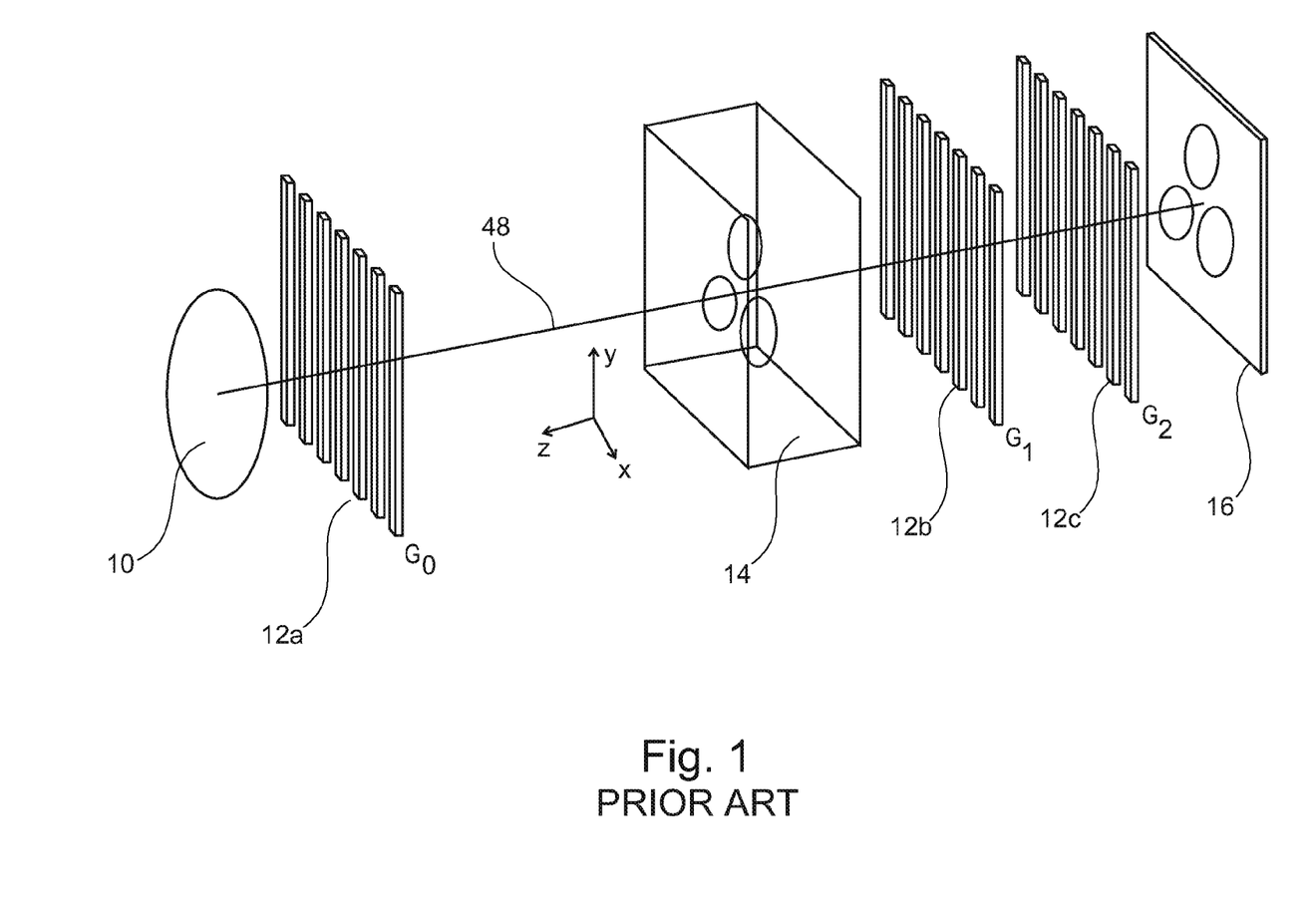
FIG. 1 shows a schematic representation of the physical principle of phase-contrast imaging.

FIG. 1 shows a schematic representation of phase-contrast imaging. Source grating 12a is situated next to X-ray source 10 for generating spatially coherent X-radiation 48. Said X-Radiation 48 is penetrating object 14, subsequently passing through source grating 12b and analyzer grating 12c to ultimately arrive at X-ray detector 16. Source grating 12b and analyzer grating 12c are displaced relative to one another by a fraction of the grating periodicity to perform phase stepping. In each phase stepping state, x-ray image information may be acquired by X-ray detector 16, for obtaining an intensity-modulation with respect to the grating position for each single pixel.

Using phase-contrast imaging technology ultimately results in more than one image information type from one examination. In particular, at least four different types of images may be calculated from the acquired raw data, resulting in at least four different image information types.

Only one image type, the amplitude, attenuation or absorption image type, resembles known X-ray images from conventional technology. All other image types may have different properties and may thus look unfamiliar to an observer familiar with regular absorption X-ray images.

US 2010/0220834 A1 describes superposition of absorption images and phase-contrast images.

SUMMARY OF THE INVENTION

One object of the present invention may be seen in providing a preferred combination of different image information types into one resulting image.

This object may be achieved by the subject-matter of the independent claims.

Preferred embodiments of the present invention are described in the dependent claims.

Phase-contrast imaging techniques usually provide several images in parallel among which there is one image indicative of the attenuation of the sample, while another image is indicative of the refraction of the X-rays by the sample. At least for workflow reasons, there may be a desire to combine different phase-contrast based imaging modalities into as few, preferably only one, image presented to a user, e.g. a radiologist, to speed up evaluation of the acquired images. Such a combination, in particular of attenuation and phase information, shall be performed in a way that is both noise optimal and further has the property of preserving the nature of the attenuation image as much as possible, while reducing noise and/or improving resolution, so that the final image visually corresponds to a conventional absorption X-ray image. The latter assures that a user, e.g. a radiologist, is presented with an image he is already familiar with.

Accordingly, it may be considered relevant to extract relevant image information from the entirety of acquired images or image types and subsequently combine them in as few as possible, preferably one, image without reducing the information content of the image data.

In this regard, differential phase-contrast images may be considered to comprise a better contrast-to-noise ratio (CNR) for high spatial frequencies than absorption images, while providing information at lower NSR at low spatial frequencies. Accordingly, at least with regard to absorption image information and differential phase-contrast image information, the resulting composite image may preferably make use of high frequency information from the differential phase-contrast image data whereas preferably makes use of low frequency information from the attenuation image data. Further or other types of image information may also be considered as well, e.g. a scattering image information or de-coherence image information, which could also be used to correct image regions in the composite image for which a fusion algorithm or a method according to the present invention may have caused image artifacts, e.g. due to locally increasing small angle scattering and, as a result, less reliable phase information. Also, in image visualization algorithms, de-coherence information may be used as a colour overlay highlighting structures in areas of an object to be examined, which produce particularly strong scattering of X-rays.

Aspects, features and advantages of the present invention may further be derived from the detailed description of preferred embodiments described hereinafter, which are explained with reference to the following drawings. Like elements may be referred to as like reference numerals.

The figures are not drawn to scale, however may depict qualitative proportions.

BRIEF DESCRIPTION OF THE DRAWINGS

FIGS. 5A-E show a further exemplary combination of different image information types according to the present invention.

DETAILED DESCRIPTION OF PREFERRED EMBODIMENTS

One possibility to obtain combined image information is based on the concept of splitting image information of a first and a second image information type in the spatial frequency domain into a plurality of distinct sub-bands, i.e. each sub-band corresponding to a defined spatial frequency range. Such a splitting may e.g. be performed by employing a Laplacian pyramid process.

The respective frequency sub-bands of image information may be analyzed, e.g. with regard to their contrast-to-noise ratio, may be weighed, in particular depending upon the determined signal-to-noise ratio, and may subsequently be added or re-combined, at least depending on the weighting factor of the respective sub-band, to ultimately obtain a single combined image, combining relevant information in a signal-to-noise ratio optimized manner of two or more different image information types.

Figure 2A:
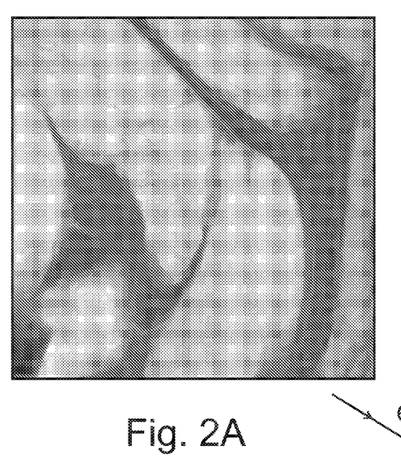
FIGS. 2A-C show an exemplary combination of different image information types according to the present invention.
Figure 2B:
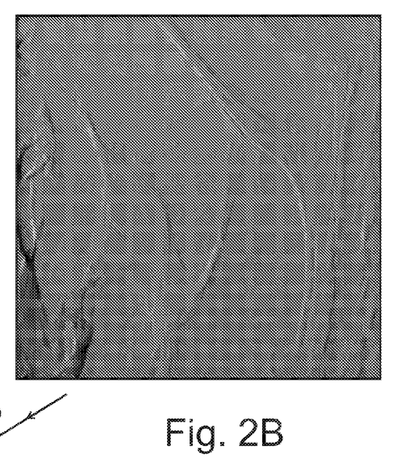
Figure 2C:
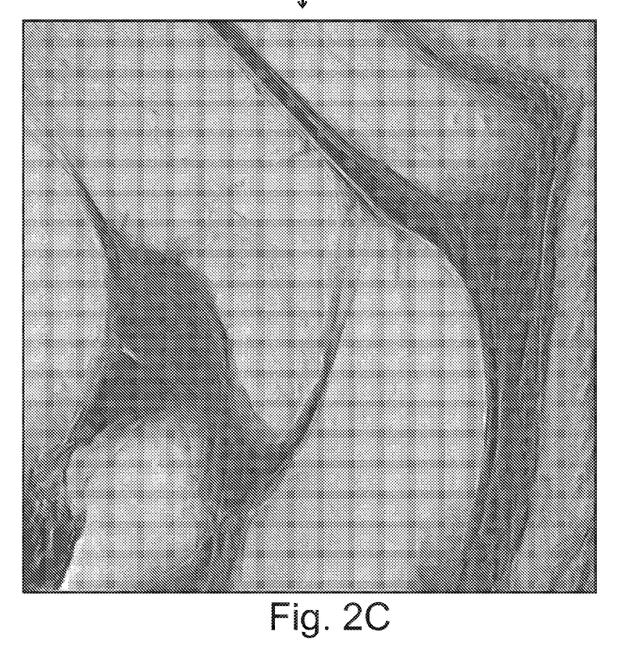

FIG. 2A shows an absorption contrast image while FIG. 2B shows a corresponding differential phase-contrast image. While the absorption contrast image may be considered to look like a regular X-ray image, the differential phase-contrast image mainly depicts image information having high spatial frequencies. Both images FIG. 2A,B are combined into FIG. 2C, substantially corresponding to a superposition of some high frequency bands of the differential phase-contrast image information into the absorption image information.

Such a combination may be considered to be similar to the regular absorption contrast image but may be considered to be superior with regard to edge enhancement of the amplitude image due to the signal-to-noise ratio in the differential phase-contrast image information being higher. FIG. 2B already presents fine edges, thus employing high spatial frequency sub-bands of the differential phase-contrast image of FIG. 2B combined with the absorption contrast image 2A leads to an edge enhancement, which will not increase the overall noise level of the combined image.

Upon taking a sequence of phase-contrast image information, at least two images of different image type may be determined. Subsequently, these two images are split into multi-resolution image sets comprising N sub-bands i, each sub-band having a defined spatial frequency range.

Subsequently weight factors $\alpha_i$ and $\beta_i$ are determined for each sub-band image. $\alpha_i$ and $\beta_i$ may be considered to be parameters for the subsequent image reconstruction of a single combined image.

The reconstruction mathematically is performed by employing equation 1.

$$out_i = \sum_{i=0}^{N} \alpha_i \cdot \text{Filter1}_i + \beta_i \cdot \text{Filter2}_i \qquad \text{Equation 1}$$

The Filter elements may be high-pass (HP), low-pass (LP), band-pass (BP) as well as notch (N) filter elements. The above notation indicates that different filters are to be applied to the image information in all sub-bands i of image 1 and image 2.

The weight factors $\alpha_i$ and $\beta_i$ may e.g. be dependent on the type of image information as well as the contrast-to-noise ratio of the respective sub-band.

In case further or additional image information types are to be employed as well, at the output, additional terms may be incorporated into the sum, e.g. Filter $3_i$, Filter $4_i$, using further weighting factors $\gamma_i$, $\delta_i$ etc.

The resulting combined image thus combines the properties of the two input images, using individual advantages of the respective image information type.

The multi-resolution images, i.e. the individual sub-band images of the individual image information types may be obtained by e.g. Laplace decomposition or wavelet decomposition.

Upon reconstruction or recombination, individual sub-bands of the individual images may e.g. be colour-coded.

Figure 3:
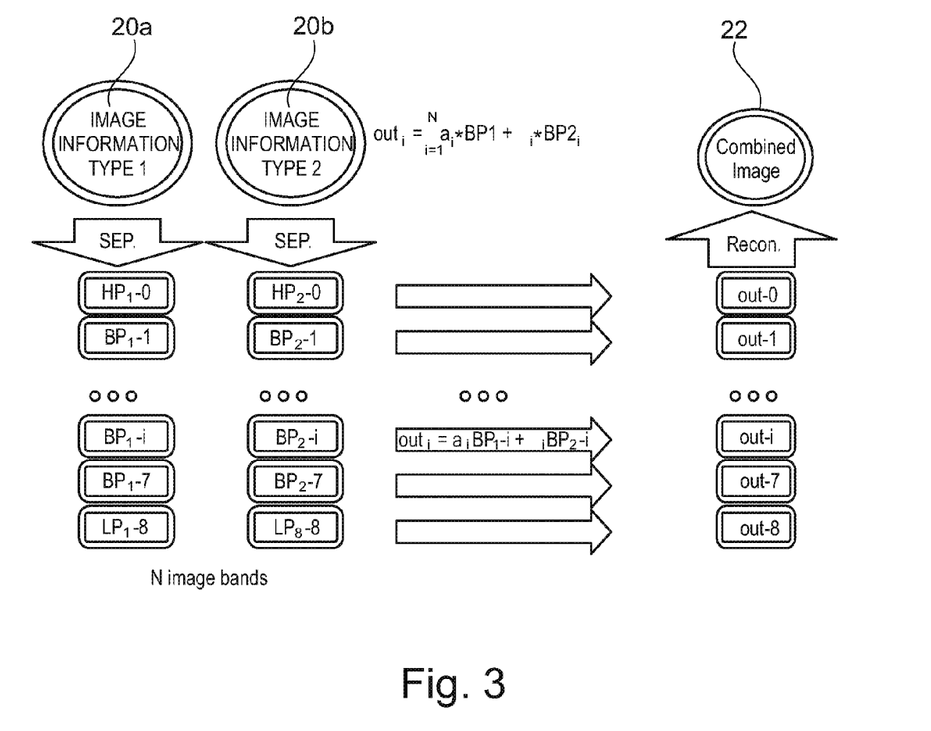
FIG. 3 shows a block diagram of an exemplary implementation of the method according to the present invention, FIGS. 4A-4J' show an exemplary frequency dependent segmentation of different image information types according to the present invention.

FIG. 3 shows a block diagram of an exemplary implementation of the method according to the present invention.

Each individual image information type 1 20*a* and 2 20*b* may be separated into individual sub-bands, e.g. by Laplace decomposition, substantially corresponding to filter elements using exemplarily a high pass filter $HP_1$-0, a low pass filter element $LP_1$-8 and seven band-pass filter elements $BP_1$-1 . . . 7. A similar decomposition is performed with regard to image information type 2 employing filter elements $HP_2$-0, $BP_2$-1 . . . 7 and $LP_2$-8, ideally corresponding, at least to the properties of, to the respective filter elements associated with image information type 1.

Each sub-band is weighed by weight factors $\alpha_i$, $\beta_i$ ($\gamma_i$, $\delta_i$ . . . ), thereby exemplarily obtaining 9 output sub-bands out-0 to out-8. These output bands are subsequently reconstructed into a combined image 22.

Figure 4:
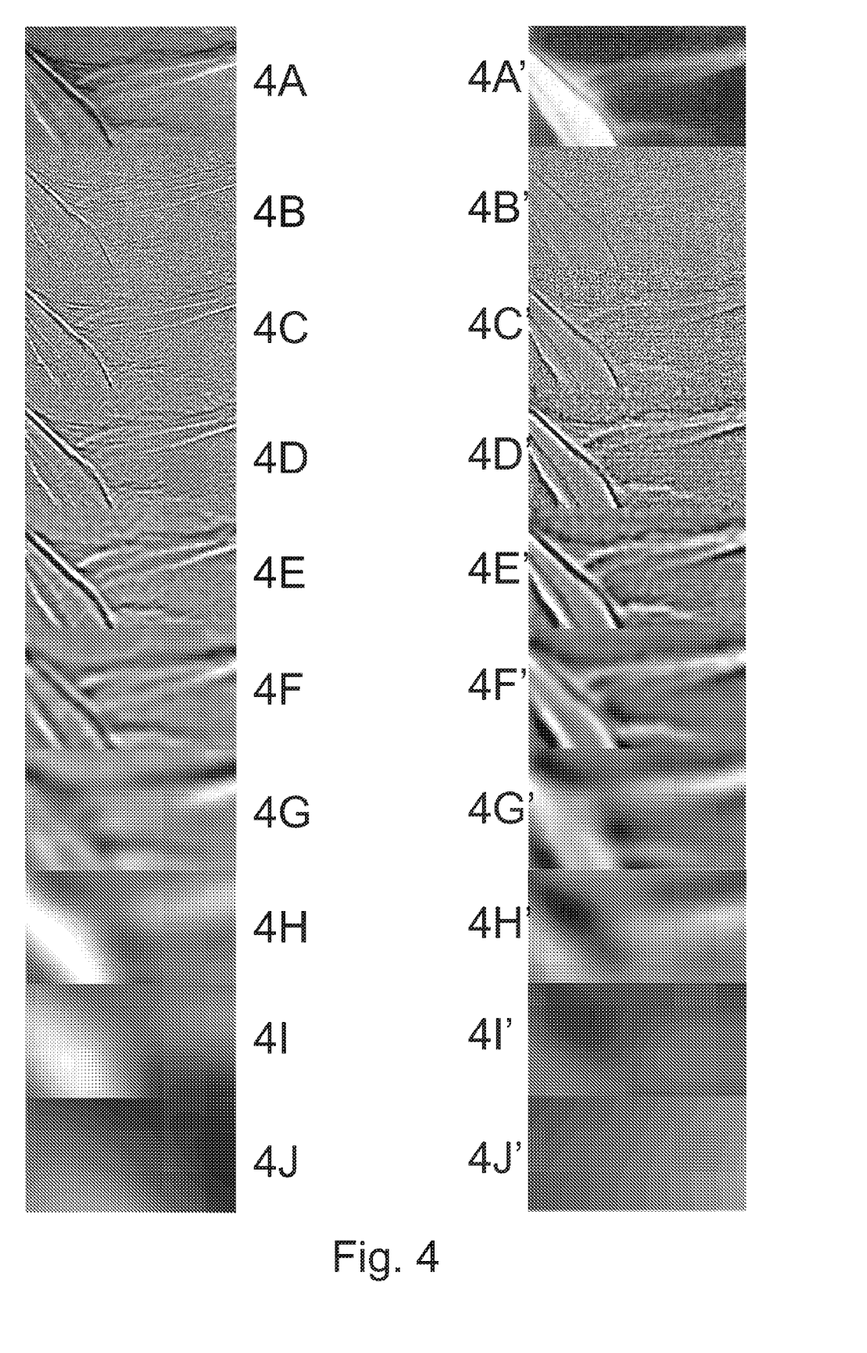

FIGS. 4A-4J show 10 frequency bands of an amplitude image, respectively, while FIGS. 4A'-4J' show 10 frequency bands of a phase-contrast image, respectively. The spatial frequencies of the 10 bands in shown in the individual pictures are decreasing from FIG. 4A/A' (i.e., corresponding to band 1) to FIG. 4J/J' (corresponding to band 10). As may be taken from FIGS. 44A-4J and FIGS. 4A'-4j', bands 1 to 4 exhibit a better contrast-to-noise ratio in the phase-contrast images shown in FIGS. 4A'-4D', while bands 8 to 10 exhibit a better contrast-to-noise ratio in the amplitude images shown in FIGS. 4H-4J, for example. Bands 5 to 7 substantially correspond to equivalent images shown in FIGS. 4E-4G and 4E'-4G', respectively.

The individual sub-images may subsequently be weighed with weight factors $\alpha_i$ and $\beta_i$, e.g. depending on their signal-to-noise ratio with regard to the respective sub-image of the other image information type, to determine a preferred recombination of individual sub-band images.

Grating-based differential phase-contrast imaging may be employed as well with regard to a computed tomography system. An according measurement provides conventional projections of the imaginary part of the object's refractive index as well as differential projections of the real part. Both projections are obtained by processing the intensities measured during a phase stepping phase for each detector pixel. In case detector cross-talk can be neglected, said would lead to white noise in the projections.

Both types of projections may be employed for reconstruction of the spatial distribution of the real refractive index and the imaginary refractive index by employing a filtered back-projection. Here, the imaginary part is reconstructed using a ramp filter, corresponding to $H(k)=|k|$ in the frequency domain, whereas the real part is reconstructed using a Hilbert filter, corresponding to $H(k)=\text{sign}(k)$ in the frequency domain. The very different spectral shapes of the filters however lead to very different noise power spectra in the reconstructed images.

Figure 5A:
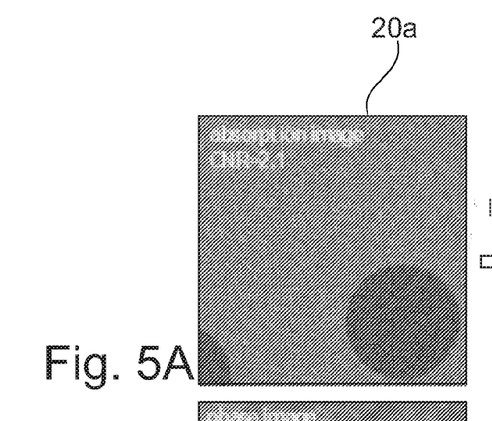
Figure 5B:
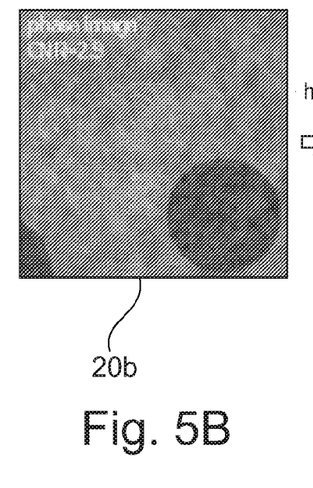

FIG. 5A shows an absorption contrast image, i.e. the imaginary part of the refractive index, while FIG. 5B shows a phase-contrast image, i.e. the real part of the refractive index. Even by a visual comparison of FIGS. 5A and 5B, the differences in noise depicted in the respective figures may be visually deduced. The associated normalized noise power spectra of FIGS. 5A and B may be taken from FIG. 6.

Figure 6:
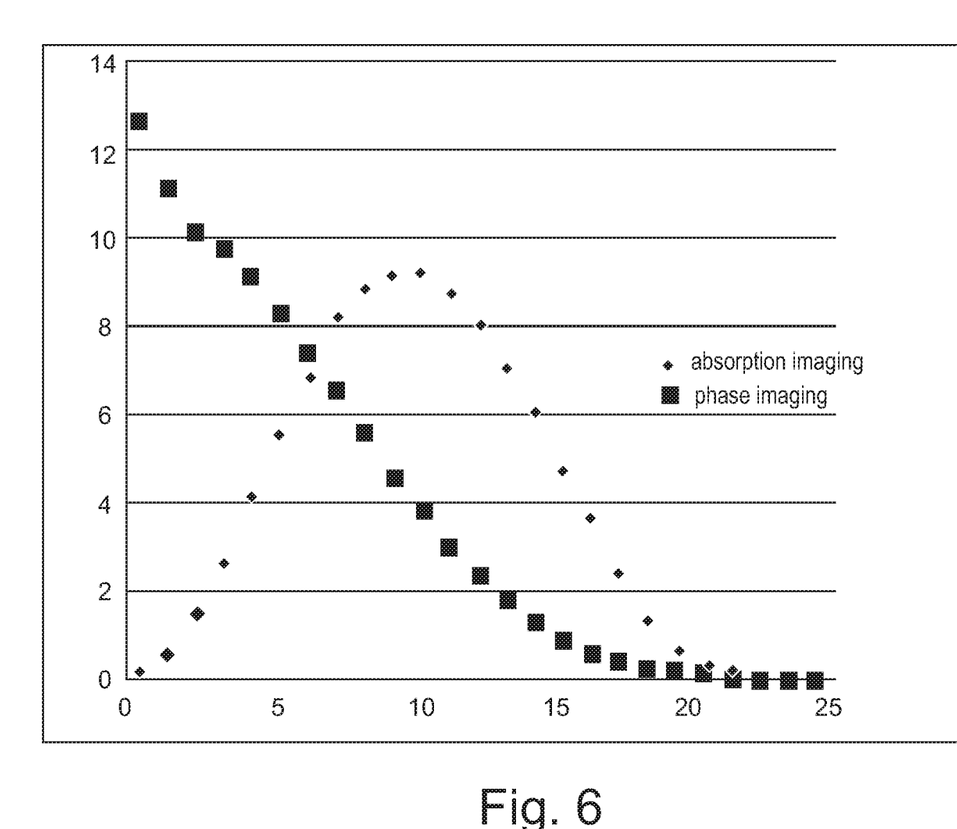
FIG. 6 shows exemplary noise in reconstructed absorption and phase-contrast image information.

The unit on the x-axis is line-pairs/cm, while the y-axis depicts the noise-power spectrum for an empty CT image of the attenuation and an empty CT image of the refractive index.

At least approximately, both the absorption contrast image and the phase-contrast image may be considered to be proportional to the local electron density in the object to be examined. This allows both images to show the same physical quantity using the same contrast after proper energy dependent rescaling of the images. Such a rescaling subsequently allows combining both images while optimizing signal-to-noise ratio.

To achieve this, the absorption contrast image is low pass filtered with L(k), while the phase-contrast image is high pass filtered with H(k), a filter element complementary to the low pass filter applied to the absorption contrast image. A filter having a resulting optimal signal-to-noise ratio may be obtained from the noise power spectrum of the absorption contrast image and the phase-contrast image of FIG. 5A,B. Such filters would have the shape in accordance with equations 2a,b.

$$L(k) = \frac{S_p(k)}{S_p(k)+S_a(k)}; H(k) = \frac{S_a(k)}{S_p(k)+S_a(k)} \quad \text{Equation 2a, b}$$

wherein $S_a(k)$ corresponds to the noise power spectrum of the absorption contrast image, and $S_p(k)$ corresponds to the noise power spectrum of the phase-contrast image.

The filter shapes L(k), H(k) according to equations 2a,b may be considered to be the best-case shapes. A further implementation would be to determine said filter shapes pre-computed based on a dedicated acquisition system and acquisition parameters as well as calibration measurements.

The filters may also contain further modifications to achieve a desired spatial resolution in the images. In a preferred embodiment, the filter operation may be part of the reconstruction process by modifications of the ramp and the Hilbert filter, respectively. In other words, these filters employed in the image domain may also be applied, with appropriate modifications, in the projection domain, where they would have to be combined with the ramp filter and Hilbert filter, respectively.

Figures 5C, 5D, 5E:
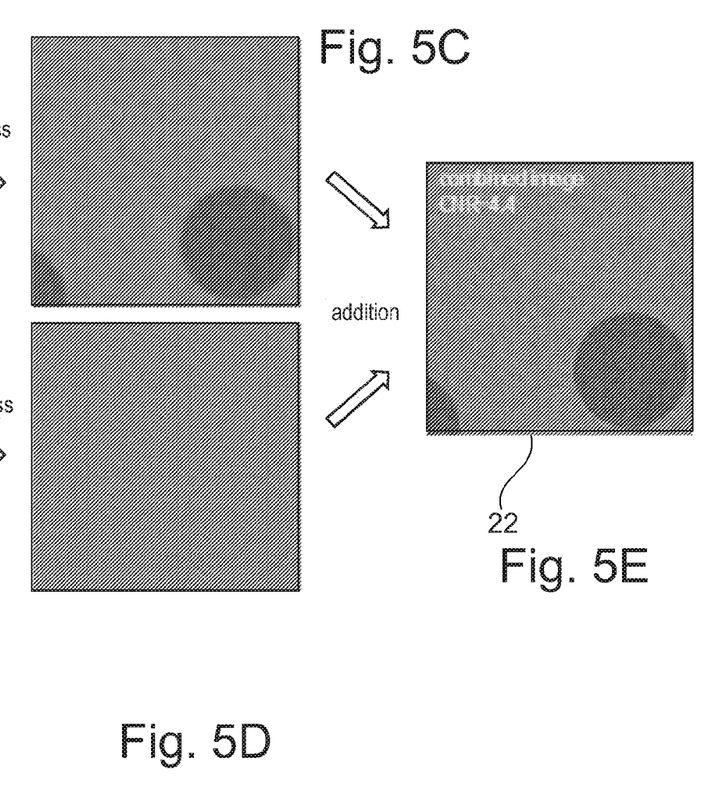

The signal-to-noise ratio optimized filtering and combination is depicted in FIGS. 5C-E. The absorption contrast image of FIG. 5A exemplarily comprises a contrast to noise ratio CNR=2.1 and is low pass filtered to obtain an image according to FIG. 5C. The phase-contrast image of FIG. 5B, comprises a CNR=2.9 and is high pass filtered to obtain an image according to FIG. 5D. Both images FIG. 5C, D are subsequently added or combined to obtain the combined image FIG. 5E, exemplarily having a CNR=4.4.

In the following, a generic approach to combine differential phase image information as well as attenuation image information from phase-contrast imaging setups is provided in Fourier space. Said method allows correctly taking into account the differential nature of the phase image by the choice of an appropriate filter in the Fourier domain, which also compensates the differentiation step inherent to the nature of the phase-contrast imaging.

The algorithm can be considered to consist of 4 major steps:
1. Global rescaling of the differential phase image to correspond to the gradient of the attenuation image
2. 1D Fourier Transformation of both images perpendicular to the gratings trench structures.
3. Noise-optimal, frequency dependent, combination of all Fourier coefficients
4. Fourier Back-Transformation An aspect of the present invention pertains to differential phase-contrast imaging, where an attenuation image, a differential phase-contrast image as well as a scattering image are generated at the same time from the same acquired image information. However, the method according to the present invention may as well be applied to other phase-contrast imaging techniques.

Attenuation image information and differential phase-contrast image information may be considered as image information pertaining to the line integrals of the linear attenuation of the sample and the gradient of the line integrals of the refractive index of the sample in the direction perpendicular to the X-ray beam and the orientation of the grating trenches, respectively. The present patent application assumes that attenuation and refraction may be transformed into each other by a mere scaling of the respective other quantity. More generally, a non-linear transfer function between $\mu$ and $\delta$ should be employed.

In the light of this assumption to obtain a noise optimal combination of different image information types, the Fourier amplitudes in one dimension of the lines of the two images are related to each other via the conventional relation between a function and its derivative and may thus be combined by two frequency depending weighting factors, which add up to "1". A fused image is subsequently obtained by Fourier back-transformation, leading to image information, which features both reduced noise as well as higher contrast at high frequencies.

An optimal combination of absorption contrast image information and differential phase-contrast image information may be taken from the following equations.

In this regard, the following symbols are employed:
f(x, y) attenuation image information
g(x, y) differential phase-contrast image information c scaling constant relating attenuation and phase of an object to be examined. The constant C may be considered a free parameter in the algorithm. However, its value may be motivated by the physical ratio between the average attenuation refractive index decrement over the energies represented in the X-ray spectrum. Also, c may be determined from the image information itself, e.g. in Fourier space, by a least square fit between the gradient of the attenuation image information and the differential phase information.

$F(k_x, y)$ 1D Fourier transform of $f(x, y)$ with respect to x
$G(k_x, y)$ 1D Fourier transform of $g(x, y)$ with respect to x
$k_x$ corresponding Fourier coordinate
$\omega_1(k_x)$ optimal filter function for attenuation contribution
$\omega_2(k_x)$ optimal filter function for differential phase contribution
$\sigma_f^2$ noise of $f(x, y)$
$\sigma_g^2$ noise of $g(x, y)$
$h(x, y)$ noise optimal composite image/combined image information
$H(k_x, y)$ 1D Fourier transform of $h(x, y)$ with respect to x In accordance with the coordinate system of FIG. 1, the X-ray beam is extending along the z-axis, while the gratings extend along the y-axis.

Attenuation image information and differential phase-contrast image information are defined according to equations 3a,b:

$$f(x, y) = \int_z \mu(x, y, z) dz; \quad \text{Equation 3a, b}$$

$$g(x, y) = \int_z \frac{\partial}{\partial x} \delta(x, y, z) dz$$

Under the assumption of equation 4a $$\mu(x,y,z) = c^{-1}\delta(x,y,z) \quad \text{Equation 4a}$$

$f(x, y)$ is differentiated according to equation 4b to relate it to $g(x, y)$:

$$\frac{\partial f(x, y)}{\partial x} = \int_z \frac{\partial}{\partial x} \mu(x, y, z) dz \quad \text{Equation 4b}$$

$$= c^{-1} \int_z \frac{\partial}{\partial x} \delta(x, y, z) dz$$

$$= c^{-1} g(x, y)$$

Subsequently, a Fourier Transform, e.g, a Fast Fourier Transform FFT along the x-axis may be implemented according to equations 5a-c:

$$F(k_x, y) = \int_{-\infty}^{\infty} f(x, y) e^{2\pi i k_x x} dx$$

$$G(k_x, y) = \int_{-\infty}^{\infty} g(x, y) e^{2\pi i k_x x} dx$$

$$= \int_{-\infty}^{\infty} c \frac{\partial f(x, y)}{\partial x} e^{2\pi i k_x x} dx$$

$$= [c e^{2\pi i k_x x} f(x, y)]_{-\infty}^{\infty} - c \int_{-\infty}^{\infty} (2\pi i k_x) f(x, y) e^{2\pi i k_x x} dx$$

It is assumed that the object function $f(x, y)$ vanishes far away from the origin so that $$G(k_x, y) = -2\pi i k_x c \int_{-\infty}^{\infty} f(x, y) e^{2\pi i k_x x} dx \quad \text{Equation 5a, b, c}$$

Under the assumption of equation 4a, $G(k_x, y)$ may be determined according to equation 6.

$$G(k_x, y) = 2\pi i k_x c F(k_x, y) \quad \text{Equation 6}$$

According to equation 6, the Fourier amplitudes of $f(x, y)$ and $g(x, y)$ are thus related by the well known relation between a function and its derivative.

Here, both $F(k_x, y)$ and $G(k_x, y)$ were obtained by the image acquisition process of phase-contrast imaging followed by a Fourier transform. Accordingly, the Fourier amplitudes are linearly combined in accordance with equation 7 to obtain the Fourier transform of the noise optimal composite image $H(k_x, y)$.

$$H(k_x, y) = \omega_1(k_x) F(k_x, y) + \omega_2(k_x) \frac{G(k_x, y)}{-2\pi i k_x c} \quad \text{Equation 7}$$

In order not to change the image signal, the following conditions need to be imposed:

Condition 1:

$$\omega_1(k_x) + \omega_2(k_x) = 1$$

together with
Condition 2:

$$\lim_{k_x \to 0} \omega_2(k_x) = 0$$

From which it directly follows that $\omega_1(k_x) = 1$; with ($\omega_1, \omega_2$ real).

The zero value of $\omega_2(k_x)$ at the origin in Fourier space guarantees that the low frequencies in the composite image information are dominated by the attenuation image information. In the following, the optimal filter functions are derived based on noise minimization in the composite image. The noise for the real and imaginary parts of $H(k_x, y)$ are given by:

$$ReH(k_x, y) = \omega_1(k_x) ReF(k_x, y) + \omega_2(k_x) \frac{1}{(-2\pi k_x c)} ImG(k_x, y)$$

$$ImH(k_x, y) = \omega_1(k_x) ImF(k_x, y) + \omega_2(k_x) \frac{1}{2\pi k_x c} ReG(k_x, y) \Rightarrow \sigma_{ReH}^2 =$$

$$\sigma_{ImH}^2 = \omega_1^2(k_x) \alpha \sigma_f^2 + \omega_2^2(k_x) \frac{1}{4\pi^2 k_x^2 c^2} \alpha \sigma_g^2$$

with $\omega_2^2(k_x) = (1 - \omega_1(k_x))^2$, $\alpha$ being a constant.
Equation 7 may now minimized with regard to $\omega_1(k_x)$ by differentiation and locating the zero.

$$\frac{\partial \sigma_{ReF}^2}{\partial \omega_1(k_x)} = 2\omega_1 \alpha \sigma_f^2 + 2(1 - \omega_1)(-1) \frac{1}{4\pi^2 k_x^2 c^2} \alpha \sigma_g^2 =$$

-continued $$0 \Rightarrow \omega_1 \left( \sigma_f^2 + \frac{\sigma_g^2}{4\pi^2 k_x^2 c^2} \right) = \frac{\sigma_g^2}{4\pi^2 k_x^2 c^2} \Rightarrow \omega_1 = \frac{1}{1 + 4\pi^2 k_x^2 c^2 \left( \frac{\sigma_f^2}{\sigma_g^2} \right)}$$

$$\omega_2 = \frac{4\pi^2 k_x^2 c^2 \left( \frac{\sigma_f^2}{\sigma_g^2} \right)}{1 + 4\pi^2 k_x^2 c^2 \left( \frac{\sigma_f^2}{\sigma_g^2} \right)}$$

The so determined filter functions automatically satisfy conditions 1 and 2.

Using the definitions $$K_0^{-2} = 4\pi^2 c^2 \frac{\sigma_f^2}{\sigma_g^2};$$

$$K_0 = \frac{1}{2\pi c} \sqrt{\frac{\sigma_g^2}{\sigma_f^2}};$$

the solutions for the filter functions may be rewritten as follows:

$$\omega_1 = \frac{1}{1 + \left( \frac{k_x}{K_0} \right)^2};$$

$$\omega_2 = \frac{\left( \frac{k_x}{K_0} \right)^2}{1 + \left( \frac{k_x}{K_0} \right)^2}$$

and the final expression of the Fourier amplitudes by:

$$H(k_x, y) = \frac{1}{1 + \left( \frac{k_x}{K_0} \right)^2} F(k_x, y) + \frac{\left( \frac{k_x}{K_0} \right)^2}{1 + \left( \frac{k_x}{K_0} \right)^2} \frac{1}{(-2\pi i k_x c)} G(k_x, y) \quad \text{Equation 8}$$

Equation 8 may also be rewritten in coordinate space.

$$h(x, y) = \int_{-\infty}^{\infty} H(k_x, y) e^{-2\pi i k_x x} dk_x$$

$$\mathcal{F}^{-1}\left( \frac{1}{1 + \left( \frac{k_x}{K_0} \right)^2} \right) \otimes f(x, y) + \mathcal{F}^{-1}\left( \frac{\left( \frac{k_x}{K_0} \right)^2}{1 + \left( \frac{k_x}{K_0} \right)^2} \frac{1}{(-2\pi i k_x c)} \right) \otimes g(x, y)$$

$$\mathcal{F}^{-1}\left( \frac{1}{1 + \left( \frac{k_x}{K_0} \right)^2} \right) = e^{-2K_0 \pi |x|} \cdot K_0 \cdot \pi$$

$$\mathcal{F}^{-1}\left( \frac{1}{-2\pi i k_x c} \cdot \frac{\left( \frac{k_x}{K_0} \right)^2}{1 + \left( \frac{k_x}{K_0} \right)^2} \right) = e^{-2K_0 \pi |x|} \cdot \frac{\text{sign}(x)}{2c}$$

to finally arrive at the composite operation in coordinate space:

$$\Rightarrow h(x, y) = \quad \text{Equation 9}$$

$$K_0 \pi e^{-2K_0 \pi |x|} \otimes f(x, y) + \frac{1}{2c} e^{-2K_0 \pi |x|} \text{sign}(x) \otimes g(x, y)$$

Accordingly, a noise optimal image h(x, y) may be obtained.

Although the foregoing calculations are exemplary for projection imaging e.g. mammography or C-arm imaging, the algorithm may be equally applied to computed tomography image information in the projection domain prior to reconstruction.

Figure 7A:
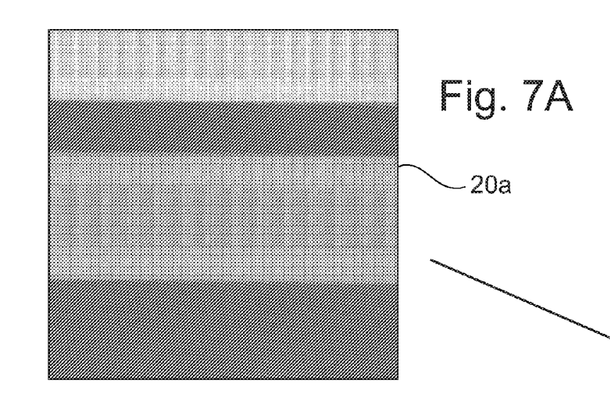
FIGS. 7A-C show a conventional attenuation image and a composition image according to an exemplary embodiment of a method according to the present invention.
Figure 7B:
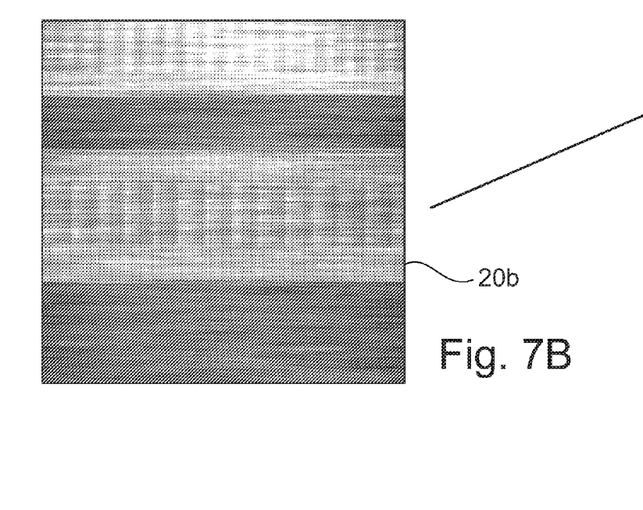
Figure 7C:
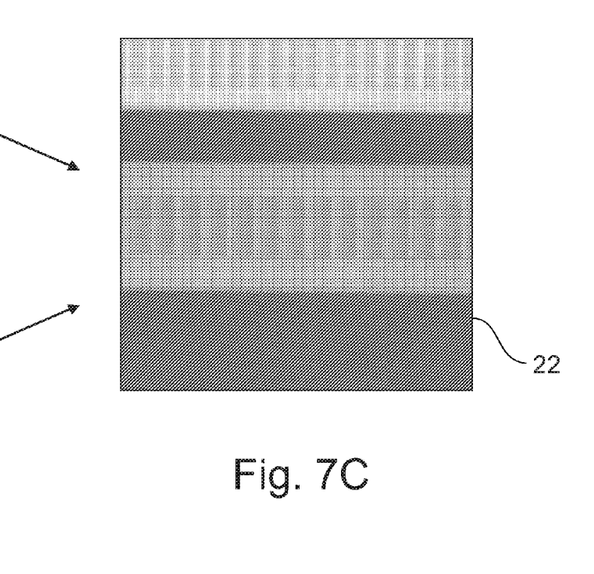

An exemplary image enhancement process may be taken from FIGS. 7A-C.

FIG. 7A depicts a conventional attenuation image, which is derived from a series of phase stepping scans of physical phantom. The associated differential phase-contrast image is depicted in FIG. 7B. Processing both FIGS. 7A and 7B in accordance with the preceding calculations provides a combined image of a composition of attenuation information and differential phase-contrast information in FIG. 7C.

FIG. 7C shows enhanced contrast, sharper edges and even suggests an improved image resolution compared to the conventional attenuation image of FIG. 7A. The noise level of FIG. 7C is also decreased, as the image combination of FIGS. 7A and 7B was performed close to noise optimal for each of the frequency components of the attenuation image FIG. 7A and the differential phase-contrast image FIG. 7B.

Figure 8:
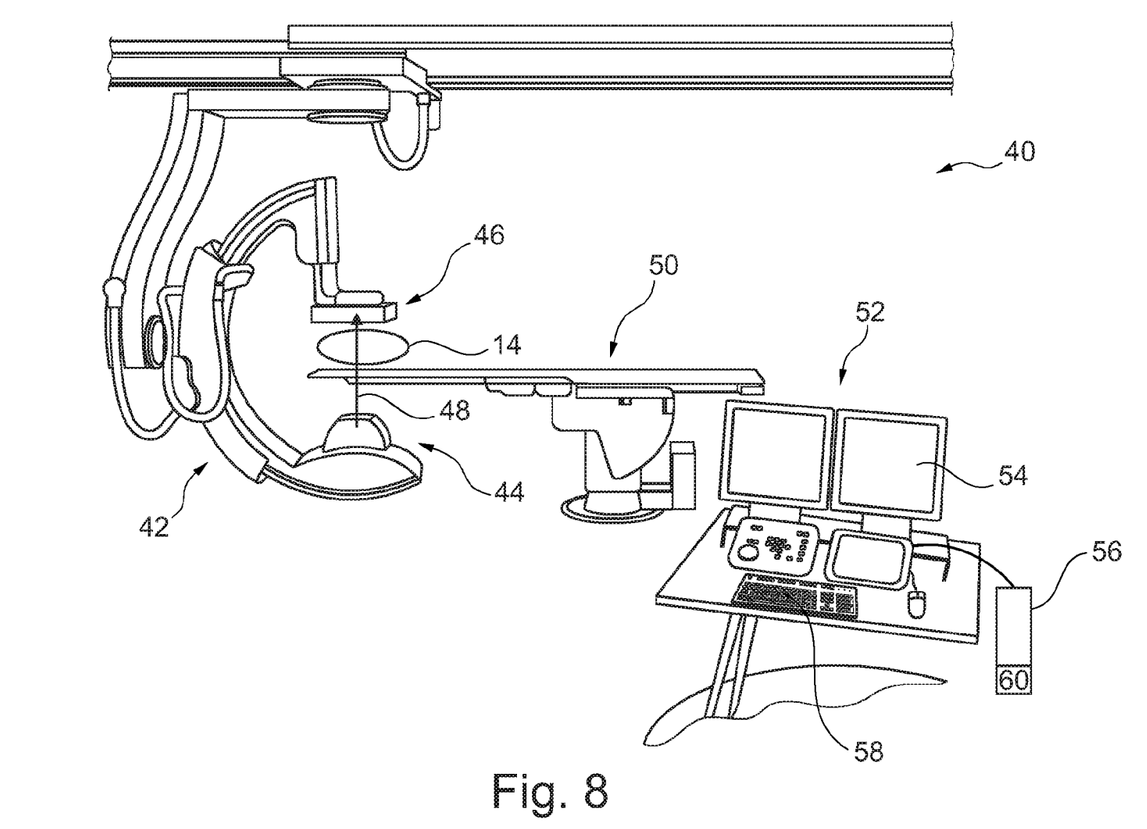
FIG. 8 shows an exemplary embodiment of a C-arm system according to the present invention.

Now referring to FIG. 8, an exemplary embodiment of a C-arm system according to the present invention is depicted.

FIG. 8 shows an exemplary embodiment of a ceiling mounted C-arm system 40 comprising C-arm 42, having an X-ray source 44 and an X-ray detector 46. Object 14 is situated on support 50 between X-ray source 44 and X-ray detector 46. X-radiation 48 is emanating from X-ray source 44, penetrating object 14 and subsequently arriving at X-ray detector 46. The additional grating elements of a phase-contrast imaging system in accordance with FIG. 1 are not depicted in detail in FIG. 8.

Control system 52, having a processing device 56, is provided for controlling image acquisition as well as provide means, e.g. within processing device 56, for performing previously described methods of the present invention.

Processing device 56 comprises storage element 60, on which image information may be stored. The processing device may be adapted to both perform the methods of the invention based on images previously acquired and subsequently stored on storage element 60 or on live image information currently acquired by C-arm system 40. Input 58 is provided for controlling image acquisition parameters as well as image reconstruction parameters.

The methods according to the present invention may be substantially be automated so that a user of an X-ray system may ultimately be provided with enhanced image information without the necessity to directly influence the image acquisition or optimization parameters.

Visualization element 54 is provided for display of image information prior and after the image enhancement process according to the present patent application to a user, e.g. a radiologist.

Figure 9:
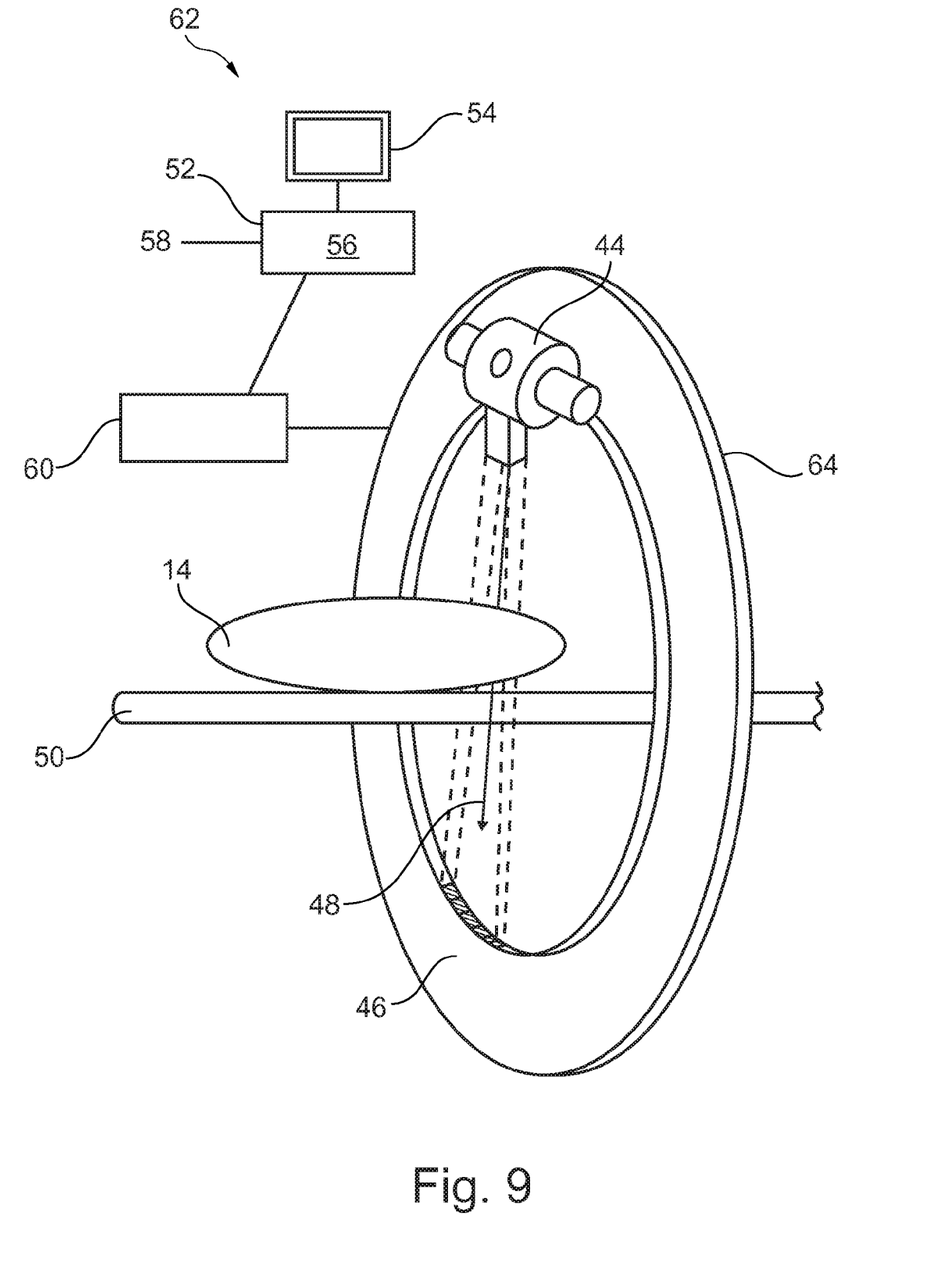
FIG. 9 shows an exemplary embodiment of a CT system according to the present invention.

Now referring to FIG. 9, an exemplary embodiment of a CT system according to the present invention is depicted.

In FIG. 9, CT system 62 is provided having an X-ray source 44 as well as an X-ray detector 46, exemplarily depicted as a one-dimensional line array, arranged on opposite sides of gantry 64. Gantry 64 is adapted for rotating both X-ray source 44 and X-ray detector 46 about object 14. Object 14 is situated on support 50 and is arranged within the X-ray beam 48. A fan shaped X-ray beam 48 is penetrating object 14, subsequently arriving at X-ray detector 46. Again, elements required for phase-contrast imaging in accordance with FIG. 1 are not depicted in FIG. 9.

Image information acquired by X-ray detector 46 is provided to control system 52, having a processing element 56. Again, processing element 56 is adapted for acquisition of X-ray image information as well as for performing the methods according to the present invention.

Image information may be acquired directly from X-ray detector 46 or may be stored on storage element 60. Input 58 is provided for controlling image acquisition parameters and method reconstruction parameters.

Both, the acquired conventional image information as well as enhanced image information or combined images in accordance with the present invention may be displayed on visualization element 54 to a user, e.g. a radiologist.

While FIGS. 8 and 9 pertain to medical imaging applications, it is to be understood that further imaging applications are feasible, e.g. baggage inspection or quality control inspection.

Figure 10:
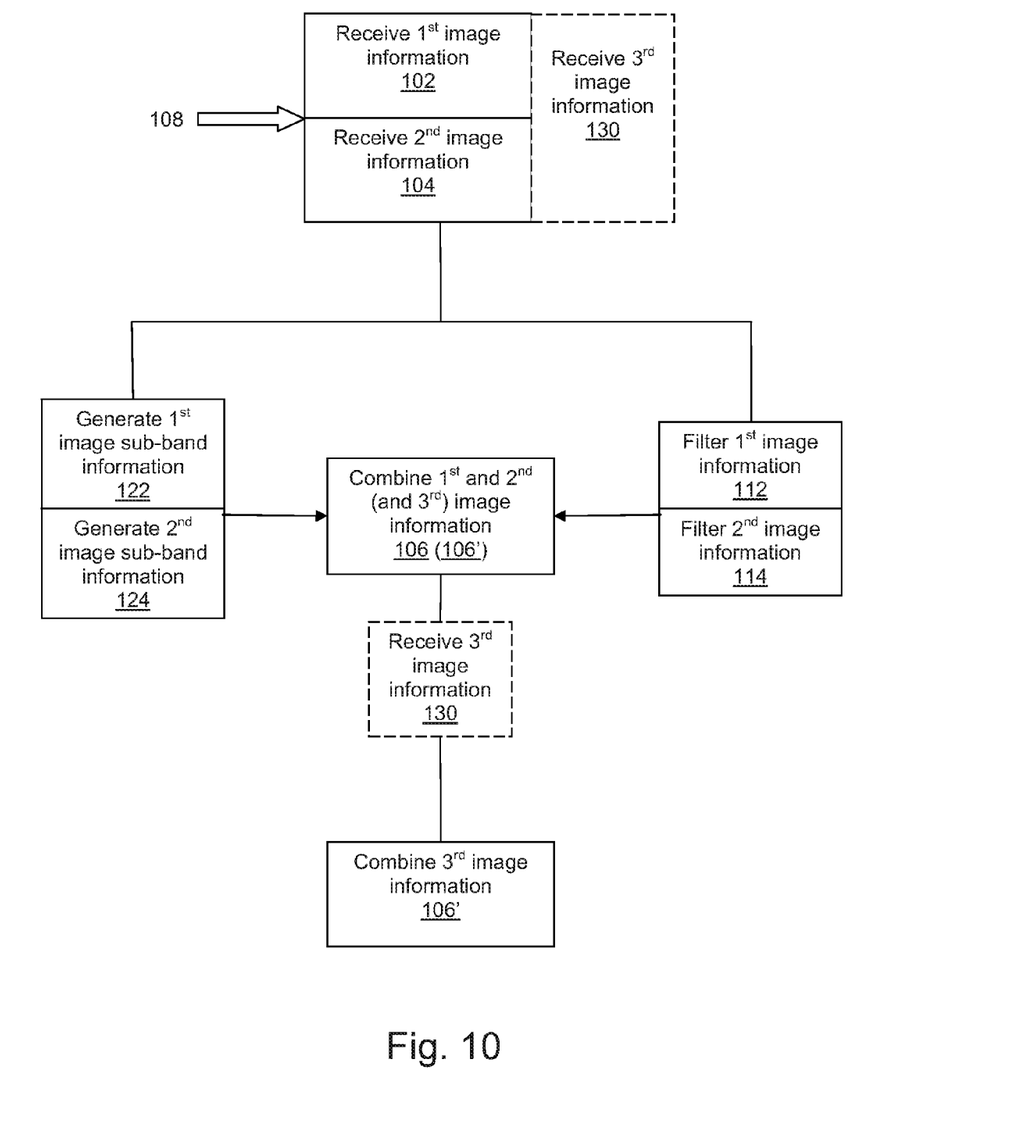
FIG. 10 shows an exemplary embodiment of the method for image processing in X-ray imaging of an object according to the present invention.

Now referring to FIG. 10, an exemplary embodiment of the method for image processing in X-ray imaging of an object according to the present invention is depicted.

FIG. 10 shows a method 100 for image processing in X-ray imaging of an object comprising the steps receiving 102 of first image information of the object of a first image information type and receiving 104 second image information of the object of a second image information type. The first image information and the second image information are of different types.

Receiving may comprise obtaining pre-acquired and stored image information but also receiving image information currently obtained by an X-ray system. First and second image information may be received 108 by phase-contrast image information containing both or further first and second image information types, wherein from the phase-contrast information the first image information and the second image information is determined 102, 104.

The first image information and the second image information are combined 106 to obtain combined image information 22 of the object, wherein the combination of the first image information and the second image information is a frequency dependent combination, depending on the spatial frequency of the first image information and the second image information. In other words, individual parts of the first image information and second image information, the parts depending on a respective spatial frequency, are employed while combining 106.

Previous to combining 106, the first image information may be filtered 112 with a first frequency filter element, while the second image information may be filtered 114 with a second frequency filter element. Subsequently, the filtered first image information and the filtered second image information may again be combined 106.

However, not only a single complementary filter element pair may be employed but also a plurality of filter elements, in particular complementary filter elements, which generate 122 a plurality of first image sub-band information and generate 124 a plurality of second image sub-band information. The sub-band information, after individual processing, e.g. weighing, may be combined 106 to obtain the combined image information 22 of the object.

Third image information of a third image information type may be received 130 either concurrently with the first and second image information or after combining 106 of the first and second image information. Subsequently the first, the second and the third image information may be combined 106', or the third image information may be combined 106' with the already combined first and second image information.

LIST OF REFERENCE SIGNS

10 X-ray source
12a,b,c Source grating, phase grating analyzer grating
14 Object
16 X-ray detector
20a,b First, second image (information)
22 Combined image (information)
40 C-arm system
42 C-arc
44 X-ray source
46 X-ray detector
48 X-radiation
50 Support
52 Control system
54 Visualization element
56 Processing device
58 Input element
60 Storage element
62 CT system
64 Gantry
100 Method for image processing in X-ray imaging
102 STEP: Receiving/determining first image information
104 STEP: Receiving/determining second image information
106,106' STEP: Combining
108 STEP: Receiving phase-contrast image information
112 STEP: Filtering first image information
114 STEP: Filtering second image information
122 STEP: Generating a plurality of first image sub-band information
124 STEP: Generating a plurality of second image sub-band information
130 STEP: Receiving third image information

The invention claimed is:

1. A method for processing images obtained by X-ray imaging of an object, comprising receiving first image information of the object of a first image information type;
receiving second image information of the object of a second image information type, wherein the first image information type is attenuation image information and the second image information type is one of differential phase contrast image information, scatter image information, and de-coherence image information;
filtering the first image information with a first frequency-filter element;
filtering the second image information with a second frequency-filter element;
wherein the first filter element and the second filter element are configured as complementary filter elements; and
combining the filtered first image information and the filtered second image information to obtain combined image information of the object;

wherein the combined image information is frequency dependent according to spatial frequencies of the first image information and the second image information.

2. The method according to claim 1, wherein the first filter element and the second filter element comprise a filter shape in accordance with $$F_1(k) = \frac{S_2(k)}{S_1(k) + S_2(k)};$$
$$F_2(k) = \frac{S_1(k)}{S_1(k) + S_2(k)}$$

wherein $F_1(k)$ and $F_2(k)$) are filter shapes, and $S_1(k)$ and $S_2(k)$) and noise power spectra of the first image information and the second image information, respectively.

3. The method according to claim 1; further comprising:
generating a plurality of first image sub-band information by splitting the first image information into sub-bands in the spatial frequency domain;
generating a plurality of second image sub-band information by splitting the second image information into sub-bands in the spatial frequency domain;
wherein the sub-bands of the first image sub-band information correspond to the sub-bands of the second image sub-band information; and
combining the plurality of first image sub-band information and the plurality of second image sub-band information to obtain combined image information of the object;
wherein each sub-band is weighed with a weight factor prior to combining; and
wherein the weight factors of a corresponding sub-band of the first image information and the second image information are dependent on the signal-to-noise ratio (SNR) of the respective first image sub-band information and the second image sub-band information.

4. The method according to claim 1, wherein the combined image information is determined in accordance with equation $$h(x, y) = K_0 \pi e^{-2K_0\pi|x|} \otimes f(x, y) + \frac{1}{2c} e^{-2K_0\pi|x|} \text{sign}(x) \otimes g(x, y)$$

or $$H(k_x, y) = \frac{1}{1 + \left(\frac{k_x}{K_0}\right)^2} F(k_x, y) + \frac{\left(\frac{k_x}{K_0}\right)^2}{1 + \left(\frac{k_x}{K_0}\right)^2 (-2\pi i k_x c)} G(k_x, y)$$

wherein
$f(x, y)$ corresponds to the first image information;
$F(k_x, y)$ corresponds to the 1D Fourier transform of $f(x, y)$ with respect to x;
$g(x, y)$ corresponds to the second image information;
$G(k_x, y)$ corresponds to the 1D Fourier transform of $g(x, y)$ with respect to x;
$k_x$ corresponds to a respective Fourier coordinate;
$h(x, y)$ corresponds to noise optimal composite image/combined image information;
$H(k_x, y)$ corresponds to the 1D Fourier transform of $h(x, y)$ with respect to x;
c corresponds to a scaling factor between the first image information and the second image information, and is estimated from expected $\lambda/\delta$ ratios and/or from the images via a least-square-fit in Fourier space;

$$K_0 = \frac{1}{2\pi c} \sqrt{\frac{\sigma_g^2}{\sigma_f^2}};$$

$\sigma_f^2$ corresponds to noise of the first image information; and
$\sigma_g^2$ corresponds to noise of the second image information.

5. The method according to claim 1, further comprising:
receiving third image information of the object of a third image information type, wherein the third image information type is different from the first image information type and the second image information type; and
further combining the third image information with the first image information and the second image information to obtain combined image information of the object;
wherein combining the first image information, the second image information and the third image information is a frequency dependent combination, depending on the spatial frequency of the first image information, the second image information and the third image information.

6. The method according to claim 1, wherein the first frequency-filter element and the second frequency-filter element are adapted comprising a filter shape ($F_1(k)$, $F_2(k)$) dependent on the noise power spectra ($S_1(k)$, $S_2(k)$) of the first image information and the second image information.

7. A method for image processing in X-ray imaging of an object; the method comprising
receiving first image information of the object of a first image information type;
receiving second image information of the object of a second image information type, wherein the second image information type is different from the first image information type;
filtering the first image information with a first frequency-filter element;
filtering the second image information with a second frequency-filter element;
wherein the first frequency-filter element and the second frequency-filter element are configured as complementary filter elements; and
combining the filtered first image information and the filtered second image information to obtain combined image information of the object;
wherein the combination of the filtered first image information and the filtered second image information is a frequency dependent combination, depending on spatial frequencies of the first image information and the second image information, wherein the first frequency-filter element and the second frequency-filter element are adapted comprising a filter shape ($F_1(k)$, $F_2(k)$) dependent on the noise power spectra ($S_1(k)$, $S_2(k)$) of the first image information and the second image information, and
wherein receiving the first and second image information comprises:
receiving phase contrast image information;
determining from the phase contrast image information the first image information; and
determining from the phase contrast image information the second image information.

8. An imaging system, comprising:
an x-ray source configured to generate radiation for penetrating an object;
an x-ray detector configured to detect radiation that passes through the object for acquiring image data of the object, the image data providing first information of the object of a first image information type and second information of the object of a second image information type different from the first image information type, wherein the first image information type is attenuation image information, and the second image information type is one of differential phase contrast image information, scatter image information, and de-coherence image information; and
a processor configured to:
  receive the first image information of the object of the first image information type and the second image information of the object of the second image information type;
  filter the first image information with a first frequency-filter;
  filter the second image information with a second frequency-filter, the first and second frequency-filters being complementary filters; and
  combine the filtered first image information and the filtered second image information to obtain combined image information of the object;
wherein the combined image information of the object comprises a frequency dependent combination, depending on the spatial frequency of the first image information and second image information.

9. The system of claim 8, further comprising:
a display adapted for visually providing at least the combined image information of the object to a user.

10. The imaging system according to claim 8, wherein the radiation further passes through a source grating and an analyzer grating for acquiring the image data of the object.

11. The imaging system according to claim 10, wherein the source grating and the analyzer grating are displaced relative to one another by a fraction of the grating periodicity to perform phase stepping.

* * * * *